US009445990B2

(12) United States Patent
Lane et al.

(10) Patent No.: US 9,445,990 B2
(45) Date of Patent: Sep. 20, 2016

(54) TNF INHIBITOR FORMULATION FOR USE IN IMPLANTABLE INFUSION DEVICES

(75) Inventors: Deanna S. Lane, Golden Valley, MN (US); Charlene X. Yuan, Woodbury, MN (US); Jianwei Li, Woodbury, MN (US); Lanchi T. Le, Lake Elmo, MN (US)

(73) Assignee: Medtronic, Inc., Minneapolis, MN (US)

( * ) Notice: Subject to any disclaimer, the term of this patent is extended or adjusted under 35 U.S.C. 154(b) by 675 days.

(21) Appl. No.: 13/252,745

(22) Filed: Oct. 4, 2011

(65) Prior Publication Data

US 2012/0088713 A1 Apr. 12, 2012

Related U.S. Application Data

(60) Provisional application No. 61/390,412, filed on Oct. 6, 2010.

(51) Int. Cl.
*A61K 9/00* (2006.01)
*A61K 47/26* (2006.01)
*A61K 38/00* (2006.01)
*A61K 38/19* (2006.01)

(52) U.S. Cl.
CPC ............ *A61K 9/0019* (2013.01); *A61K 47/26* (2013.01)

(58) Field of Classification Search
None
See application file for complete search history.

(56) References Cited

U.S. PATENT DOCUMENTS

| | | | | |
|---|---|---|---|---|
| 4,496,689 | A | 1/1985 | Mitra | |
| 4,640,835 | A | 2/1987 | Shimizu et al. | |
| 7,056,695 | B2 | 6/2006 | Dahiyat et al. | |
| 7,101,974 | B2 | 9/2006 | Dahiyat et al. | |
| 7,144,987 | B1 | 12/2006 | Chirino et al. | |
| 7,244,823 | B2 | 7/2007 | Dahiyat et al. | |
| 7,446,174 | B2 | 11/2008 | Desjarlais et al. | |
| 7,610,156 | B2 | 10/2009 | Desjarlais et al. | |
| 7,642,340 | B2 | 1/2010 | Desjarlais et al. | |
| 7,662,367 | B2 | 2/2010 | Desjarlais et al. | |
| 8,779,094 | B2 * | 7/2014 | Johnston et al. | 530/350 |
| 2005/0265962 | A1 | 12/2005 | Desjarlais et al. | |
| 2006/0257360 | A1 | 11/2006 | Desjarlais et al. | |
| 2007/0172449 | A1 | 7/2007 | Carmichael et al. | |
| 2007/0207961 | A1 | 9/2007 | Dahiyat et al. | |
| 2008/0187509 | A1 | 8/2008 | Desjarlais et al. | |
| 2011/0033463 | A1 * | 2/2011 | Thakker et al. | 424/134.1 |

FOREIGN PATENT DOCUMENTS

| | | | |
|---|---|---|---|
| EP | 1717246 | A1 | 11/2006 |
| WO | 2006113487 | A1 | 10/2006 |

OTHER PUBLICATIONS

Ngo et al., 1994, The Protein Folding Problem and Tertiary Structure Prediction, pp. 492-495.*
Wells, Additivity of Mutational Effects in Proteins, Biochemistry, vol. 29, No. 37, 8509-8517.*
Wells, (1990), Additivity of Mutational Effects in Proteins, Biochemistry, vol. 29, No. 37, 8509-8517.*
PCT International Search Report and Written Opinion dated Dec. 23, 2011.

* cited by examiner

*Primary Examiner* — Christine J Saoud
*Assistant Examiner* — Jegatheesan Seharaseyon
(74) *Attorney, Agent, or Firm* — Mueting, Raasch & Gebhardt, P.A.

(57) ABSTRACT

A formulation for use in an implantable infusion device includes between about 5 mg/ml and about 500 mg/ml (e.g., about 10-25 mg/ml) of a TNF inhibitor polypeptide, 10 mM-25 mM of a phosphate or citrate buffer, has an ionic strength of the combined buffer and an optional salt of the equivalent of about 0.1-0.2 NaCl (e.g., about 0.15 M), 5% to 10% of a carbohydrate (e.g., trehalose or sucrose), has a pH of between 6 and 7, is fluid at room temperature and at 37° C., and has a viscosity of less than about 10 centipoise (e.g., between about 1 centipoise and 9 centipoise, between about 1 cp and about 5 cp, between about 1 cp and about 3 cp, or between about 1 cp and about 2.5 cp) at room temperature.

17 Claims, No Drawings

SEQUENCE LISTING

```
<160> NUMBER OF SEQ ID NOS: 1

<210> SEQ ID NO 1
<211> LENGTH: 233
<212> TYPE: PRT
<213> ORGANISM: Homo sapiens

<400> SEQUENCE: 1

Met Ser Thr Glu Ser Met Ile Arg Asp Val Glu Leu Ala Glu Glu Ala
1               5                   10                  15

Leu Pro Lys Lys Thr Gly Gly Pro Gln Gly Ser Arg Arg Cys Leu Phe
            20                  25                  30

Leu Ser Leu Phe Ser Phe Leu Ile Val Ala Gly Ala Thr Thr Leu Phe
        35                  40                  45

Cys Leu Leu His Phe Gly Val Ile Gly Pro Gln Arg Glu Glu Phe Pro
```

-continued

| | | | | | | | | | | | | | | | |
|---|---|---|---|---|---|---|---|---|---|---|---|---|---|---|---|
| | 50 | | | | 55 | | | | 60 | | | | | | |
| Arg | Asp | Leu | Ser | Leu | Ile | Ser | Pro | Leu | Ala | Gln | Ala | Val | Arg | Ser | Ser |
| 65 | | | | | 70 | | | | | 75 | | | | | 80 |
| Ser | Arg | Thr | Pro | Ser | Asp | Lys | Pro | Val | Ala | His | Val | Val | Ala | Asn | Pro |
| | | | | 85 | | | | | 90 | | | | | 95 | |
| Gln | Ala | Glu | Gly | Gln | Leu | Gln | Trp | Leu | Asn | Arg | Arg | Ala | Asn | Ala | Leu |
| | | | 100 | | | | | 105 | | | | | 110 | | |
| Leu | Ala | Asn | Gly | Val | Glu | Leu | Arg | Asp | Asn | Gln | Leu | Val | Val | Pro | Ser |
| | | 115 | | | | | 120 | | | | | 125 | | | |
| Glu | Gly | Leu | Tyr | Leu | Ile | Tyr | Ser | Gln | Val | Leu | Phe | Lys | Gly | Gln | Gly |
| | 130 | | | | | 135 | | | | | 140 | | | | |
| Cys | Pro | Ser | Thr | His | Val | Leu | Leu | Thr | His | Thr | Ile | Ser | Arg | Ile | Ala |
| 145 | | | | | 150 | | | | | 155 | | | | | 160 |
| Val | Ser | Tyr | Gln | Thr | Lys | Val | Asn | Leu | Leu | Ser | Ala | Ile | Lys | Ser | Pro |
| | | | | 165 | | | | | 170 | | | | | 175 | |
| Cys | Gln | Arg | Glu | Thr | Pro | Glu | Gly | Ala | Glu | Ala | Lys | Pro | Trp | Tyr | Glu |
| | | | 180 | | | | | 185 | | | | | 190 | | |
| Pro | Ile | Tyr | Leu | Gly | Gly | Val | Phe | Gln | Leu | Glu | Lys | Gly | Asp | Arg | Leu |
| | | 195 | | | | | 200 | | | | | 205 | | | |
| Ser | Ala | Glu | Ile | Asn | Arg | Pro | Asp | Tyr | Leu | Asp | Phe | Ala | Glu | Ser | Gly |
| | 210 | | | | | 215 | | | | | 220 | | | | |
| Gln | Val | Tyr | Phe | Gly | Ile | Ile | Ala | Leu | | | | | | | |
| 225 | | | | | 230 | | | | | | | | | | |

TNF INHIBITOR FORMULATION FOR USE IN IMPLANTABLE INFUSION DEVICES

RELATED APPLICATIONS

This application claims the benefit of priority to U.S. Provisional Patent Application No. 61/390,412, filed on Oct. 6, 2010, which application is hereby incorporated herein by reference to the extent that it does not conflict with the disclosure presented herein.

FIELD

This application relates, among other things, to injectable formulations containing a TNF inhibitor, such as formulations that are stable in, compatible with, and deliverable via an implantable infusion device.

BACKGROUND

A number of therapeutic agents have been developed and formulated for use in implantable infusion devices. For example, preservative-free morphine sulfate sterile solution has been formulated for chronic intraspinal (epidural and intrathecal) infusion in the treatment of chronic intractable pain; preservative-free ziconotide sterile solution has been used for chronic intrathecal infusion for the management of severe chronic pain; LIORESAL® Intrathecal (baclofen injection) has been developed for chronic intrathecal infusion for the management of severe spasticity; and floxuridine (FUDR) or methotrexate have been used for chronic intravascular infusion for the treatment of primary or metastatic cancer.

Prior to chronic delivery in an implantable infusion device, a number of studies are performed to determine whether the drug and other components of the formulation are stable in the device (e.g., at 37° C. for 30 days) and compatible with the device (e.g., do not corrode, gum up, or cause fatigue of device components). The formulation may also be adjusted to ensure that the infusion device will properly pump and dispense the fluid (e.g., the viscosity is in a range that will allow long term delivery by the infusion device).

Regardless of the agent to be delivered, obtaining a suitable formulation for chronic delivery via an implantable infusion device can present a number of challenges. The challenges are typically more numerous with large molecules, such as polypeptides, as opposed to small molecules such as the morphine, ziconitide, baclofen, floxuride and methotrexate mentioned above. With large molecules, the tendency to agglomerate and prevent proper flow through an infusion device presents some challenges, as does increased viscosity, which can result in increased wear on the pumping mechanism or the inability to pump.

One class of large molecule therapeutic agents that may be of great interest for use in implantable infusion devices is tumor necrosis factor (TNF) inhibitors, such as TNFalpha inhibitors. In many cases, TNF-alpha inhibitors are antibodies to TNF-alpha, such as inflixamib (REMICADE), adalimumab (HUMERIA), certolizumab (CIMZIA), and golimab (SIMPONI), or circulating receptor fusion proteins, such as enanercept (ENBREL). Steed et al. have described rational design of dominant-negative TNF variants (Science, vol. 301, p. 1895, 2003). Using this approach, Zalevsky et al. reported dominant negative inhibitors of soluble TNF that attenuate experimental arthritis without suppressing innate immunity to infection (J. Immunol, vol. 179, p. 1872, 2007).

These agents, which include XPro1595 (XENP1595), may be good candidates for delivery via an implantable infusion device for treatment of TNF-related diseases. However, suitable formulations for use in such implantable devices are lacking.

SUMMARY

The present disclosure, among other things describes formulations containing dominant-negative TNF inhibitors, which formulations are injectable. The formulations, in embodiments, are suitable for use in implantable infusion devices.

In various embodiments, an injectable formulation includes between about 5 mg/ml and about 500 mg/ml (e.g., about 5 mg/ml to about 50 mg/ml or about 10-25 mg/ml) of a TNF inhibitor polypeptide, 10 mM-25 mM of a phosphate or citrate buffer, has an ionic strength of the combined buffer and an optional salt of the equivalent of about 0.1-0.2 NaCl (e.g., about 0.15 M), 5% to 10% of a carbohydrate (e.g., trehalose or sucrose), has a pH of between 6 and 7, is fluid at room temperature and at 37° C., and has a viscosity of less than about 10 centipoise (e.g., between about 1 cp and 9 cp or between about 1 cp and 3 cp) at room temperature.

Such formulations may be used with chronically implanted infusion devices, allowing for targeted delivery of the TNF inhibitors, which may result in improved efficacy and reduced side effects relative to systemic delivery. This and other advantages will become evident upon reading the description herein.

DETAILED DESCRIPTION

The following description illustrates various embodiments. It is to be understood that other embodiments are contemplated and may be made without departing from the scope or spirit of the present invention. Thus, the following description is not to be taken in a limiting sense.

All scientific and technical terms used in this application have meanings commonly used in the art unless otherwise specified. The definitions provided herein are to facilitate understanding of certain terms used frequently herein and are not meant to limit the scope of the present disclosure.

As used herein, a "TNF inhibitor polypeptide" is a polypeptide (i.e., containing two or more amino acids joined by a peptide bond) that inhibit the effect of tumor necrosis factor (TNF), such as TNF alpha. The TNF inhibitor polypeptide may be an antibody, a receptor fusion protein, a dominant-negative inhibitor, or the like.

Embodiments of the present disclosure provide injectable formulations containing a TNF inhibitor. In embodiments, such formulations are stable in, compatible with, and deliverable by the implantable infusion device. When such formulations are delivered by an implantable infusion device, the device and formulation may be used for any suitable purpose for which study or use of the effects of the formulation delivered by the infusion device is desired. For example, formulations containing a TNF inhibitor may be used in studies to determine or elucidate (a) the effect of the TNF inhibitor on a molecule, cell, tissue, organ, organism, or combination thereof; (b) the mechanism of action of the TNF inhibitor, (c) the properties of the TNF inhibitor, a solution containing the TNF inhibitor, or a combination thereof; and (d) the like.

The formulations containing a TNF inhibitor may also be used as therapy to treat a disease state responsive to the TNF inhibitor such as an inflammatory or immunological disorder. Some examples of specific diseases for which TNF inhibitors may be beneficial include spondyloarthritis, rheumatoid arthritis, inflammatory bowel diseases, sepsis and septic shock, Crohn's Disease, psoriasis, graft versus host disease (GVHD) and hematologic malignancies, such as multiple myeloma (MM), myelodysplastic syndrome (MDS) and acute myelogenous leukemia (AML), cancer and the inflammation associated with tumors, peripheral nerve injury or demyelinating diseases, Alzheimers disease, Parkinson's disease, inflammatory bowel disease (e.g., ulcerative colitis or Crohn's disease), pain, or the like. In the context of the present disclosure, the terms "treat", "therapy", and the like are meant to include methods to alleviate, slow the progression, prevent, attenuate, or cure the treated disease.

TNF Inhibitor

In various embodiments, a fluid formulation including a TNF inhibitor is provided. Any suitable TNF inhibitor may be employed. In various embodiments, the TNF inhibitor is a rationally designed dominant-negative TNF inhibitor (see, Steed et al., Science, vol. 301, p. 1895, 2003). In some embodiments, the TNF-alpha inhibitor is a TNF variant having one or more of the following amino acid substitutions: VIM, R31C, C69V, Y87H, C101A, and A145R as compared to wild-type TNF-alpha.

By "variant TNF-alpha" is meant the variant TNF-alpha differs from the corresponding wild type protein by at least 1 amino acid. Thus, a variant of human TNF-alpha is compared to human sequence (GenBank accession no. Caa26669 (SEQ ID NO:1); embl accession X02910.1, which sequences associated with these accession numbers are hereby incorporated herein by reference in their respective entireties to the extent that they do not conflict with the disclosure presented herein); and a mammalian variant is compared to the corresponding wild-type mammalian TNF-alpha. As used herein variant TNFalpha includes monomers, dimers or trimers. Included within the definition of "variant TNF-alpha" are competitive inhibitor TNF-alpha variants. By "competitive inhibitor TNF-alpha variants" is meant variants that compete with naturally occurring TNF-alpha for binding to the TNF receptor without activating TNF signaling, thereby limiting the ability of naturally occurring TNF-alpha to bind and activate the TNF receptor. By "inhibits the activity of TNF-alpha" and grammatical equivalents is meant at least a 10% reduction in wild-type TNF-alpha activity relative to homotrimeric variant TNF-alpha or heterotrimeric variant: wild-type TNF-alpha (e.g. allelelic variants), more preferably at least a 50% reduction in wild-type TNF-alpha activity, and even more preferably, at least 90% reduction in wild-type TNF-alpha activity. In some embodiments, there is a selective inhibition of the activity of soluble TNF-alpha versus transmembrane TNFalpha, and in some cases, the activity of soluble TNF-alpha is inhibited while the activity of transmembrane TNF-alpha is substantially or completely maintained.

In many embodiments, a formulation includes a variant TNF alpha selected from the group consisting of XENP268 XENP344, XENP345, XENP346, XENP550, XENP551, XENP557, XENP1593, XENP1594, and XENP1595, as described in U.S. Published Patent Application, Publication No. US 2008/0187509, entitled "Pharmaceutical Compositions for the Treatment of TNF-alpha Related Disorders", published on Aug. 7, 2008, and naming Desjarlais et al. as inventors, which published patent application is hereby incorporated by reference in its entirety to the extent that it does not conflict with the present disclosure. As disclosed in US 2008/0187509 XENP1595 corresponds to human TNF-alpha having the following amino acid substitutions relative to the wild-type sequence: VIM; R31 C; C69V; Y78H; C101A; and A145R, where the C at position 31 is PEGylated. In some embodiments, a formulation suitable for use in an implantable infusion device includes any other TNF inhibitor disclosed in US 2008/0187509.

In various embodiments, a formulation described herein includes a TNF inhibitor having 90% or more sequence identity with XENP1595, 95% or more sequence identity with XENP1595, or 98% or more sequence identity with XENP1595.

As is known in the art, a number of different programs may be used to identify whether a polypeptide has sequence identity or similarity to a known sequence. Sequence identity or similarity is determined using standard techniques known in the art, including, but not limited to, the local sequence identity algorithm of Smith & Waterman, Adv. Appl. Math., 2:482 (1981), by the sequence identity alignment algorithm of Needleman & Wunsch, J. Mol. Biol., 48:443 (1970), by the search for similarity method of Pearson & Lipman, Proc. Natl. Acad. Sci. U.S.A., 85:2444 (1988), by computerized implementations of these algorithms (GAP, BESTFIT, FASTA, and TFASTA in the Wisconsin Genetics Software Package, Genetics Computer Group, 575 Science Drive, Madison, Wis.), the Best Fit sequence program described by Devereux et al., Nucl. Acid Res., 12:387-395 (1984), all of which are hereby incorporated herein by reference in their entireties to the extent that they do not conflict with the present disclosure, preferably using the default settings, or by inspection. Percent identity may be calculated by FastDB based upon the following parameters: mismatch penalty of 1; gap penalty of 1; gap size penalty of 0.33; and joining penalty of 30, "Current Methods in Sequence Comparison and Analysis," Macromolecule Sequencing and Synthesis, Selected Methods and Applications, pp 127-149 (1988), Alan R. Liss, Inc, which is hereby incorporated herein by reference in its entirety to the extent that it does not conflict with the present disclosure. An example of a useful algorithm is PILEUP. PILEUP creates a multiple sequence alignment from a group of related sequences using progressive, pair wise alignments. It may also plot a tree showing the clustering relationships used to create the alignment. PILEUP uses a simplification of the progressive alignment method of Feng & Doolittle, J. Mol. Evol. 35:351-360 (1987); the method is similar to that described by Higgins & Sharp CABIOS 5:151-153 (1989), which are hereby incorporated herein by reference in their entireties to the extent that they do not conflict with the present disclosure. Useful PILEUP parameters including a default gap weight of 3.00, a default gap length weight of 0.10, and weighted end gaps. Another example of a useful algorithm is the BLAST algorithm, described in: Altschul et al., J. Mol. Biol. 215, 403-410, (1990); Altschul et al., Nucleic Acids Res. 25:3389-3402 (1997); and Karlin et al., Proc. Natl. Acad. Sci. U.S.A. 90:5873-5787 (1993), which are hereby incorporated herein by reference in their entireties to the extent that they do not conflict with the present disclosure. A particularly useful BLAST program is the WU-BLAST-2 program which may be obtained from Altschul et al., Methods in Enzymology, 266:460-480 (1996); http://blast.wustl/edu/blast/README.html]. WU-BLAST-2 uses several search parameters, most of which are set to the default values. The adjustable parameters are set with the following values: overlap span=1, overlap fraction=0.125, word threshold (T)=11. The HSP S and HSP S2 parameters are dynamic values and are established by the program itself depending upon the composition of the particular sequence and composition of the particular database against which the sequence of interest is being searched; however, the values may be adjusted to increase sensitivity. An additional useful algorithm is gapped BLAST, as reported by Altschul et al., Nucl. Acids Res., 25:3389-3402, which is hereby incorporated herein by reference in its entirety to the extent that it does not conflict with the present disclosure. Gapped BLAST uses BLOSUM-62 substitution scores; threshold T parameter set to 9; the two-hit method to trigger ungapped extensions; charges gap lengths of k a cost of 10+k; Xu set to 16, and Xg set to 40 for database search stage and to 67 for the output stage of the algorithms. Gapped alignments are triggered by a score corresponding to about 22 bits. A % amino acid sequence identity value is determined by the number of matching identical residues divided by the total number of residues of the "longer" sequence in the aligned region. The "longer" sequence is the one having the most actual residues in the aligned region (gaps introduced by WU-Blast-2 to maximize the alignment score are ignored). The alignment may include the introduction of gaps in the sequences to be aligned. It is understood that in one embodiment, the percentage of sequence identity will be determined based on the number of identical amino acids in relation to the total number of amino acids. Thus, for example, sequence identity of sequences shorter than that of the XENP 1595 will be determined using the number of amino acids in the shorter sequence, in some embodiments. In percent identity calculations relative weight is not assigned to various manifestations of sequence variation, such as, insertions, deletions, substitutions, etc. In some embodiments, only identities are scored positively (+1) and all forms of sequence variation including gaps are assigned a value of "0", which obviates the need for a weighted scale or parameters as described below for sequence similarity calculations. Percent sequence identity may be calculated, for example, by dividing the number of matching identical residues by the total number of residues of the "shorter" sequence in the aligned region and multiplying by 100. The "longer" sequence is the one having the most actual residues in the aligned region. Thus, those TNF inhibitors that have 90% or greater amino acid sequence identity to XENP 1595 may be shorter or longer than the amino acid sequence of XENP 1595.

TNF inhibitors may be obtained from commercial sources or may be made using recombinant techniques generally known in the art. For example, dominant negative variant TNF inhibitors may be made as described in one or more of: Steed et al., Science, vol. 301, p. 1895, 2003; Zalevsky et al., J. Immunol, vol. 179, p. 1872, 2007; and US 2008/0187509.

In some embodiments, polypeptide TNF inhibitors, such as variant TNF-alpha inhibitors, are modified to include polymers, such as polyethylene glycol ("PEG"), polypropylene glycol, or polyoxyalkylenes, e.g., in the manner set forth in U.S. Pat. No. 4,640,835; 4,496,689; 4,301,144; 4,670,417; 4,791,192 or 4,179,337, and U.S. application Ser. No. 10/956,352, filed Sep. 30, 2004, all of which are incorporated herein by reference in their entireties to the extent that they do not conflict with the present disclosure. These nonproteinaceous polymers may be used to enhance the TNF inhibitor's ability to disrupt receptor binding, in vivo stability, stability in the infusion device, or the like. In some embodiments, one or more cysteine residues are designed into the polypeptide TNF alpha inhibitor to incorporate PEGylation sites. A variety of coupling chemistries may be used to achieve PEGylation, as is well known in the art. Examples include but are not limited to, the technologies of Shearwater and Enzon, which allow modification at primary amines, including but not limited to, lysine groups and the N-terminus. See, Kinstler et al, Advanced Drug Deliveries Reviews, 54, 477-485 (2002) and M J Roberts et al, Advanced Drug Delivery Reviews, 54, 459-476 (2002), both are incorporated herein by reference in their entireties to the extent that they do not conflict with the present disclosure. Preferred methods for identifying suitable sites for either the addition or removal of putative PEGylation sites are found in U.S. application Ser. No. 10/956,352, filed Sep. 30, 2004, and U.S. application Ser. No. 11/200,444, filed Aug. 8, 2005, both are incorporated herein by reference in their entireties to the extent that they do not conflict with the present disclosure. Variant TNF inhibitors can have amino acid modifications to modulate the addition of polymer groups, such as polyethylene glycol (PEG), including the alteration of cysteine groups at positions 69 and 101 to residues that will not participate in a PEGylation reaction (e.g. C69V, C101A), and the addition of cysteine residues, such as at position 31 (e.g. R31C), to allow for precise PEGylation. These positions may be altered for other reasons as well, or can be mutated to utilize other functional groups in addition to cysteine. Any combination of these sites, or others, can be done.

In some embodiments, the TNF-inhibitor includes a non-proteinaceous polymer, such as PEG, such that the resulting molecule has a molecular weight of between about 5 kDa and 50 kDa, e.g. between about 7 kDa and 20 kDa or about 10 kDa.

Formulation

As used herein, an injectable formulation is a fluid composition at room temperature and at body temperature of the subject in which the formulation is infused. Fluid compositions include solutions, suspensions, dispersions, and the like. Solutions, suspensions, dispersions, and the like may be formulated according to techniques well-known in the art (see, for example, Remington's Pharmaceutical Sciences, Chapter 43, 14th Ed., Mack Publishing Co., Easton, Pa.), using suitable dispersing or wetting and suspending agents, such as sterile oils, including synthetic mono- or diglycerides, and fatty acids, including oleic acid.

Injectable formulations containing a TNF inhibitor may be prepared in water, saline, isotonic saline, phosphate-buffered saline, citrate-buffered saline, and the like and may optionally mixed with a nontoxic surfactant. Dispersions may also be prepared in glycerol, liquid polyethylene, glycols, DNA, vegetable oils, triacetin, and the like and mixtures thereof. Under ordinary conditions of storage and use, these preparations may contain a preservative to prevent the growth of microorganisms. Pharmaceutical dosage forms suitable for injection or infusion include sterile, aqueous solutions or dispersions or sterile powders comprising an active ingredient which powders are adapted for the extemporaneous preparation of sterile injectable or infusible solutions or dispersions. Preferably, the ultimate dosage form is a sterile fluid and stable under the conditions of manufacture and storage. A liquid carrier or vehicle of the solution, suspension or dispersion may be a solvent or liquid dispersion medium comprising, for example, water, ethanol, a polyol such as glycerol, propylene glycol, or liquid polyethylene glycols and the like, vegetable oils, nontoxic glyceryl esters, and suitable mixtures thereof. Proper fluidity of solutions, suspensions or dispersions may be maintained, for example, by the formation of liposomes, by the maintenance of the desired particle size, in the case of dispersion, or by the use of nontoxic surfactants. The prevention of the action of microorganisms can be accomplished by various antibacterial and antifungal agents, for example, parabens, chlorobutanol, phenol, sorbic acid, thimerosal, and the like. In many cases, it will be desirable to include isotonic agents, for example, sugars, buffers, or sodium chloride. Prolonged absorption of the fluid compositions can be brought about by the inclusion in the composition of agents delaying absorption—for example, aluminum monosterate hydrogels and gelatin. Excipients that increase solubility, such as cyclodextrin, may be added.

Sterile injectable compositions may be prepared by incorporating a therapeutic agent in the desired amount in the appropriate solvent with various other ingredients as enumerated above and, as desired, followed by sterilization. Any means for sterilization may be used. For example, the solution may be autoclaved or filter sterilized. In the case of sterile powders for the preparation of sterile injectable solutions, methods of preparation include vacuum drying and freeze-drying techniques, which yield a powder of the active ingredient plus any additional desired ingredient present in a previously sterile-filtered solution. Fluid compositions containing TNF-inhibitors may be sterilized by heat-treatment (e.g., autoclaving) or radiation (e.g., e-beam or gamma) in some embodiments.

The formulation may include any suitable amount of TNF inhibitor. In various embodiments, the formulation comprises between about 5 mg/ml and 500 mg/ml. For purposes of this disclosure, if the polypeptide is conjugated to other molecules, such as PEG, the weight of the polypeptide will include the weight of the moieties conjugated to the polypeptide. For example, the formulation for use in an implantable infusion device may contain between about 5 and 50 mg/ml of a TNF inhibitor, between about 10 and 50 mg/ml of a TNF inhibitor, or about 25 mg/ml of a TNF inhibitor.

It has been found that pH is important for stability of the TNF inhibitor and for the viscosity of the fluid formulation. In various embodiments, the formulation has a pH of between about 4 and 9, such as between about 4 and 8, between about 6 and 7.5, between 6.5 and 7.3, or about 7. The pH of the fluid formulation may be adjusted with an appropriate acidic or basic solution, such as 1N NaOH or 1N HCl.

In various embodiments, the TNF inhibitor formulation includes a buffer, such as a phosphate (e.g., $Na_3PO_4$) or citrate (e.g., sodium citrate) buffer. For example, a concentrated TNF inhibitor composition (including a near pure lyophilized TNF inhibitor) may be diluted in the buffer. The pH of the formulation containing the buffer and the TNF inhibitor may be adjusted as described above. The buffer may be present at any suitable concentration, such as between about 0 and 50 mM. In some embodiments, the buffer is present at a concentration of between about 5 mM and 30 mM, or about 10 mM, 15 mM or 25 mM.

The formulation may have any suitable ionic strength. The formulation may include a salt, such as NaCl, to maintain ionic strength. In various embodiments, the combined ionic strength of the formulation contributed by the buffer and one or more salts is the equivalent of the ionic strength of between about 0.1 M and 0.2 M NaCl, or about 0.15 M NaCl. For example, a formulation that includes a 25 mM $Na_3PO_4$ buffer may include 0.085M NaCl to yield a combined ionic strength of the buffer and the NaCl at an equivalent of 0.15 M NaCl.

In various embodiments, an injectable formulation includes one or more excipients for reducing gelation or viscosity. Examples of such excipients include carbohydrates and benzyl alcohol. Examples of suitable carbohydrates that may be used include D-manitol, sucrose, D(+)-trehalose dihydrate, PEG 400, PEG 1000, and glycerin. The one or more carbohydrates may be present in the formulation at any suitable cumulative concentration. For example, the carbohydrate may be present at a concentration of about 2% to about 20% by weight, such as between about 4% and 11%, or about 5%.

The resulting formulation preferably has a sufficiently low viscosity to be loaded into a reservoir of an implanted infusion device and to be delivered by the implanted infusion device. Thus, the viscosity at room temperature and at body temperature is preferably low enough to prove free flow of the fluid formulation through a refill needle or an implanted catheter. In various embodiments, the formulation has a viscosity of less than about 10 centipoise, such as between about 1 centipoise and 9 centipoise, between about 1 cp and about 5 cp, between about 1 cp and about 3 cp, or between about 1 cp and about 2.5 cp.

When the formulation is intended for direct delivery to the central nervous system (CNS) of a subject, it may be desirable to select excipients that are known to be non-toxic to neural tissue. Such excipients are well know and include phosphate buffered saline, citric acid buffers, and the like.

In embodiments where the formulation is intended for delivery to CNS, it may be desirable for the formulation to be isotonic with cerebrospinal fluid, which typically has a tonicity of about 305 microOsmolar (mOsm). For purposes of the present disclosure, a formulation having a tonicity of between about 270 mOsm and 600 mOsm, e.g. between about 290 mOsm and 320 mOsm is considered to be isotonic with cerebrospinal fluid. While such tonicities are desired, the overall ionic strength of the formulation may, in many cases, take precedence over the desire to achieve isotonicity.

Administration

Formulations according to the present disclosure may be administered to a subject through any acceptable route. For example, the fluid formulations may be administered intravenously, subcutaneously, intra-arterially, inthrathecally, epidurally, intraparenchymally, intraperitoneally, intracerebroventricularly, etc., by infusion or injection.

Preferably, a therapeutically effective dose of a TNF inhibitor is administered to a patient in need of treatment. By "therapeutically effective dose" herein is meant a dose that produces the effects for which it is administered. The exact dose will depend on the purpose of the treatment, and will be ascertainable by one skilled in the art using known techniques. In some embodiments, dosages of about 0.5 micrograms/kg to about 5 micrograms/kg are used. As is known in the art, adjustments for systemic versus localized delivery, and rate of new protease synthesis, as well as the age, body weight, general health, gender, diet, time of administration, drug interaction and the severity of the condition may be necessary, and will be ascertainable with routine experimentation by those skilled in the art.

In some embodiments, the TNF inhibitor is administered to a patient in a daily dose of between about 0.001 mg/kg/day to 100 mg/kg/day. A "patient" for the purposes of the present disclosure includes both humans and other animals, particularly mammals, and organisms. Thus, the methods are applicable to both human therapy and veterinary applications. In a preferred embodiment the patient is a mammal, such as a human. Those "in need of treatment" include mammals already having the disease or disorder, as well as those prone to having the disease or disorder, including those in which the disease or disorder is to be prevented.

Infusion Device

Any suitable infusion device may be used to deliver the formulation containing a TNF inhibitor to a patient may be used. The infusion device may include an osmotic pump, a fixed rate or variable rate pump, a piston pump, a peristaltic pump, or the like. Typically, infusion devices include reservoirs for housing the fluid formulation. A catheter is typically connected to the infusion device so that fluid from the reservoir may be pumped from the reservoir through the catheter to a targeted region of the patient. In some embodiments, the infusion device is implantable and includes a microprocessor for controlling the rate of delivery of the formulation, which may be variable. In such embodiments, the implantable infusion device may communicate and receive infusion instructions from an external device, such as a physician programmer device.

Preferably, the injectable TNF inhibitor formulation is stable in, and compatible with, the infusion device when implanted in a patient. Accordingly, the formulation and TNF inhibitor in the formulation is preferably stable at 37° C. In many embodiments, the formulation is stable at room temperature, e.g. at about 20° C. or about 25° C. In embodiments, the formulation is stable for 30 days or more at room temperature or at 37° C. In general, a formulation will be considered stable if 80% or more of the initial TNF inhibitor remains.

Summary of Selected Aspects

A first aspect is an injectable formulation of a TNF inhibitor. The formulation includes between 5 mg/ml and 500 mg/ml of a TNF inhibitor polypeptide; between 10 mM and 25 mM of a phosphate or citrate buffer; between 5% and 10% of a carbohydrate; and optionally NaCl, wherein the combined ionic strength of the buffer and the optional salt is an equivalent ionic strength of between 0.1M and 0.2M NaCl, wherein the formulation has a pH of between 6 and 7, is fluid at room temperature and at 37° C., and has a viscosity of 10 centipoise or less at room temperature.

A second aspect is a formulation of the first aspect, wherein the TNF inhibitor polypeptide is conjugated to a polymer and has a molecular weight of between 5 kilodaltons and 50 kilodaltons.

A third aspect is a formulation of the first aspect, wherein the TNF inhibitor polypeptide is conjugated to a polymer and has a molecular weight of between 7 kilodaltons and 20 kilodaltons.

A fourth aspect is a formulation of the first aspect, wherein the TNF inhibitor polypeptide is conjugated to a polymer and has a molecular weight of between about 10 kilodaltons.

A fifth aspect is a formulation of any of the second, third or fourth aspects, wherein the polymer comprises polyethylene glycol.

A sixth aspect is a formulation of any of the first five aspects, wherein the TNF inhibitor polypeptide comprises a polypeptide having one or more amino acid substitutions relative to wild-type human TNF alpha having GenBank Accession No. Caa26669, wherein the amino acid substitutions are selected from the group consisting of VIM, R31C, C69V, Y87H, C101, and A145R.

A seventh aspect is a formulation of any of the first five aspects, wherein the TNF inhibitor polypeptide comprises a TNF inhibitor polypeptide selected from the group consisting of XENP268 XENP344, XENP345, XENP346, XENP550, XENP551, XENP557, XENP1593, XENP1594, and XENP1595.

A eighth aspect is a formulation of any of the first five aspects, wherein the TNF inhibitor polypeptide comprises XENP1595.

A ninth aspect is a formulation of any of the first five aspects, wherein the TNF inhibitor polypeptide comprises a polypeptide having 90% or more sequence identity with the polypeptide sequence of XENP1595.

A tenth aspect is a formulation of any of the first nine aspects, wherein the TNF inhibitor polypeptide is present in the formulation at a concentration of between 10 mg/ml and 25 mg/ml.

An eleventh aspect is a formulation of any of the first ten aspects, wherein the carbohydrate is trehalose of sucrose.

A twelfth aspect is a formulation of any of the first ten aspects, wherein the carbohydrate is trehalose.

A thirteenth aspect is a formulation of any of the first twelve aspects, wherein the combined ionic strength of the buffer and the optional salt is an equivalent ionic strength of 0.15M.

A fourteenth aspect is a formulation of any of the first thirteen aspects, wherein the formulation has a viscosity of between 1 centipoise and 9 centipoise at room temperature.

A fifteenth aspect is a formulation of any of the first thirteen aspects, wherein the formulation has a viscosity of between 1 centipoise and 5 centipoise at room temperature.

A sixteenth aspect is a formulation of any of the first thirteen aspects, wherein the formulation has a viscosity of between 1 centipoise and 3 centipoise at room temperature.

An seventeenth aspect is a formulation of any of the first thirteen aspects, wherein the formulation has a viscosity of between 1 centipoise and 2.5 centipoise at room temperature.

A eighteenth aspect is an injectable formulation of a TNF inhibitor. The formulation includes: between 5 mg/ml and 500 mg/ml of a TNF inhibitor polypeptide, wherein the TNF inhibitor polypeptide comprises XENP1595 conjugated to polyethylene glycol and has a molecular weight of between 7 kilodaltons and 20 kilodaltons; between 10 mM and 25 mM of a phosphate or citrate buffer; between 5% and 10% of a carbohydrate, wherein the carbohydrate is selected from the group consisting of trehalose and sucralose; and optionally NaCl, wherein the combined ionic strength of the buffer and the optional salt is an equivalent ionic strength of between 0.1M and 0.2M NaCl, wherein the formulation has a pH of between 6 and 7, is fluid at room temperature and at 37° C., and has a viscosity of 10 centipoise or less at room temperature.

A nineteenth aspect is a formulation of any of the first eighteen aspects, wherein the formulation is stable at room temperature 30 days or more.

A twentieth aspect is a formulation of any of the first nineteen aspects, wherein the formulation is stable at 37° C. for 30 days or more.

In the following Examples, studies performed and results obtained for determining a suitable formulation containing a TNF inhibitor for use in an implantable infusion device are described. In particular, the studies were performed using XPEN 1595. However, it will be understood that other polypeptide TNF inhibitors may be substituted for XPEN 1595 in accordance with the teachings presented herein.

EXAMPLES

In the following Examples, XPro 1595 (Xencor), which is a PEGylated XENP 1595, having a molecular weight of about 10 kDa was used.

Example 1

Evaluation of pH

As many cyclic peptides, XENP 1595 is formed using a disulfide bond to increase its conformational rigidity; providing receptor selectivity and to increase potency. However, degradation of the disulfide bond in formulation can lead to a loss of structural stability and biological activity of the peptide. The degradation of this peptide is dependent on pH and buffer concentration.

Accordingly, formulation pH plays an important role in the solubility and stability of peptide/protein formulations. pH is carefully selected to provide chemical and physical stability, and sufficient solubility. The first major experiment described herein evaluates the pH of the formulation.

Table 1 summarizes the buffers and pH ranges used in the experiment.

TABLE 1

Preparation of Formulation Buffers and pH

| Salt | Buffer pH | Buffer Concentration (M) | Charge of Cation (+) | Charge of Anion (−) | Ionic Strength from Buffer (not NaCl) | NaCl to Maintain Constant Strength for 25 mL Volume NaCl (M) | Weight (g) |
|---|---|---|---|---|---|---|---|
| Saline | | 0.15 | 1 | 1 | 0.15 | 0.15 | |
| Phosphate | 7 | 0 | 1 | 2 | 0 | 0.15 | 0.219 |
| | | 0.005 | 1 | 2 | 0.0125 | 0.1375 | 0.201 |
| | | 0.01 | 1 | 2 | 0.025 | 0.125 | 0.183 |
| | | 0.025 | 1 | 2 | 0.0625 | 0.0875 | 0.128 |
| Phosphate | 6 | 0 | 1 | 2 | 0 | 0.15 | 0.219 |
| | | 0.005 | 1 | 2 | 0.0125 | 0.1375 | 0.201 |
| | | 0.01 | 1 | 2 | 0.025 | 0.125 | 0.183 |
| | | 0.025 | 1 | 2 | 0.0625 | 0.0875 | 0.128 |
| Phosphate | 8 | 0 | 1 | 2 | 0 | 0.15 | 0.219 |
| | | 0.005 | 1 | 2 | 0.0125 | 0.1375 | 0.201 |
| | | 0.01 | 1 | 2 | 0.025 | 0.125 | 0.183 |
| | | 0.025 | 1 | 2 | 0.0625 | 0.0875 | 0.128 |
| Phosphate | 3 | 0 | 1 | 1 | 0 | 0.15 | 0.219 |
| | | 0.005 | 1 | 1 | 0.005 | 0.145 | 0.212 |
| | | 0.01 | 1 | 1 | 0.01 | 0.14 | 0.205 |
| | | 0.025 | 1 | 1 | 0.025 | 0.125 | 0.183 |
| Phosphate | 2 | 0 | 1 | 1 | 0 | 0.15 | 0.219 |
| | | 0.005 | 1 | 1 | 0.005 | 0.145 | 0.212 |
| | | 0.01 | 1 | 1 | 0.01 | 0.14 | 0.205 |
| | | 0.025 | 1 | 1 | 0.025 | 0.125 | 0.183 |
| Phosphate | 11 | 0 | 1 | 3 | 0 | 0.15 | 0.219 |
| | | 0.005 | 1 | 3 | 0.025 | 0.125 | 0.183 |
| | | 0.01 | 1 | 3 | 0.05 | 0.1 | 0.146 |
| | | 0.025 | 1 | 3 | 0.125 | 0.025 | 0.037 |
| Carbonate | 10 | 0 | 1 | 2 | 0 | 0.15 | 0.219 |
| | | 0.005 | 1 | 2 | 0.0125 | 0.1375 | 0.201 |
| | | 0.01 | 1 | 2 | 0.025 | 0.125 | 0.183 |
| | | 0.025 | 1 | 2 | 0.0625 | 0.0875 | 0.128 |
| Carbonate | 9 | 0 | 1 | 2 | 0 | 0.15 | 0.219 |
| | | 0.005 | 1 | 2 | 0.0125 | 0.1375 | 0.201 |
| | | 0.01 | 1 | 2 | 0.025 | 0.125 | 0.183 |
| | | 0.025 | 1 | 2 | 0.0625 | 0.0875 | 0.128 |
| Citrate | 4 | 0 | 1 | 1 | 0 | 0.15 | 0.219 |
| | | 0.005 | 1 | 1 | 0.005 | 0.145 | 0.212 |
| | | 0.01 | 1 | 1 | 0.01 | 0.14 | 0.205 |
| | | 0.025 | 1 | 1 | 0.025 | 0.125 | 0.183 |
| Citrate | 5 | 0 | 1 | 2 | 0 | 0.15 | 0.219 |
| | | 0.005 | 1 | 2 | 0.0125 | 0.1375 | 0.201 |
| | | 0.01 | 1 | 2 | 0.025 | 0.125 | 0.183 |
| | | 0.025 | 1 | 2 | 0.0625 | 0.0875 | 0.128 |

In the compositions presented in Table 1, NaCl is added to maintain a constant ionic strength (0.154 m) for all buffers. A total of 58 buffers (phosphate buffers prepared with sodium phosphate and sodium phosphate dibasic) were prepared @ pH 2, 3, 4, 5, 6, 7, 8, 9, 10, and 11. The concentrations of buffers were 0, 5, 10, and 25 mM in sodium chloride. The buffers were then used to dilute XPro1595 stock peptide solution (~100 mg/mL) to ~1 mg/mL solution. They were then stored on HPLC sample tray @ 40° C. to allow a continuous monitoring by HPLC analysis.

For HPLC analysis, 1 mg/mL XenP1595 in extreme low and high pH buffers (pH 2, 3, 10, and 11) were first tested. Many injection cycles (T0 to T12) were run continuously for 4 days (every sample on the tray is injected in each cycle, and each injection is about 10 min). At this point, pH 10 and 11 buffers were dropped since their chromatograms showed quick and high degradation. Extra sets of these samples were also prepared and saved in 4, 37, and −20° C. Later on, they were all stored in 4° C. for additional information, if needed.

The HPLC separation conditions were:

Column: Agilent—Zorbax SB-C8, 5 μm, 4.6×50 mm

Mobile phase: A: 0.1% Perchloric Acid in DI water

Mobile phase B: Acetonitrile

Mobile phase gradient: Start at 10% B going up to 70% B in 5 minutes, hold at 70% B for 2 minutes, then back to 10% B at 7.01 minutes and complete the run at 10 minutes.

Column temperature: 60° C.

Sampler temperature: 40° C.

Flow rate: 1 mL/min

Injection volume: 5 μl

Run time: 10 minutes

Next, HPLC analysis of 1 mg/mL XenP1595 in neutral pH buffers (pH 4, 5, 6, 7, 8, and 9) was started. Extra sets of these samples were also prepared and saved at 4, 37, and −20° C. The samples in HPLC auto-sampler were run for many cycles (T0 to T35) for about 3 weeks. The caps of HPLC vials were changed to new caps regularly to prevent evaporation and all samples were kept in the auto-sampler at 40° C. all the time. At this point, by comparing the HPLC chromatographs, pH 2 and 3 buffers were dropped. After a few more days of analysis of the 1 mg/mL samples in neutral pH buffers, pH 8 and 9 buffers now were dropped also.

The pH 4, 5, 6, and 7 buffers were considered the best candidates. Higher concentration formulations at 10 mg/mL XenP1595 were prepared in those buffers and were subjected to force degradation in 50° C. oven. These samples were HPLC analyzed daily for the first week, then one time for the $1^{st}$ and $2^{nd}$ week time points. At 2 weeks conclusion, pH 4, 5, 6, and 7 buffers with 10 mg/mL XenP1595 were stable. The ones with pH 4, 5, 6 were better (in term of height and impurity peaks) than that of pH 7 buffer.

So, buffers 4-3 (25 mM NaCitrate pH 4), 5-3 (25 mM NaCitrate pH 5), and 7-3 (25 mM $Na_3PO_4$ pH 7-No pH adjustment) were used to prepare 25 and 50 mg/mL XenP1595 sample solutions in HPLC vials (stored in 50° C. oven). They were injected to HPLC for analysis of T0, T1D, T2D, T3D, and then T6D. After every injection, the caps for the vials were changed to prevent the evaporation and the samples were put in 50° C. After the T0 injection, the samples became thicker, and the chromatograph showed uneven peak heights and widths. It is noted that with only 1 μL injection, accuracy would not have been reliable.

During analysis for the 25 and 50 mg/mL samples, 1 mg/mL diluted samples from the 25 and 50 mg/mL were also prepared and analyzed. The 50 mg/mL samples became gel and could not be withdrawn to prepare 1 mg/mL samples. Accordingly, only 1 mg/mL samples from 25 mg/mL samples were prepared and analyzed. The 25 mg/mL XenP1595 in pH 7 buffer was easiest to withdraw compared to the other 2 samples of 25 mg/mL. We suspect that the 25 mg/mL samples in buffers 4 and 5 became more viscous than that of the sample in pH 7. The HPLC analysis also showed that the 1 mg/mL sample prepared from the 25 mg/mL sample in pH 7 gave taller peak compared to the other two. At 50° C., 25 mg/mL sample in pH7 buffer appeared to be most promising.

Thus, pH 7 was initially chosen as the most suitable pH for further development.

All samples of 10, 25, and 1 mg/mL dilution from 25 mg/mL were then kept in 50° C. for another 2 weeks. They were checked weekly until then.

10 mg/mL samples in pH 4, 5, 6, 7 buffers at 50° C. for 3 weeks were analyzed, and 1 mg/mL samples in pH 4, 5, 6, and 7 at 40° C. (on auto sampler) for 6 weeks were analyzed. After the HPLC run was completed, pHs of the 10 mg/mL samples were measured. In general, pHs of phosphate and citrate buffers did not change very much. However, the pH of 0.15 M NaCl buffers did change a lot. The conclusion at this point was, although the buffers with pH 5 and 6 gives the best looking chromatograms in term of absorbance and peak shapes, the viscosity is higher than pH 7. With pH 7 buffers, the samples were more stable and did not get to gellation as much as pH 5 and pH 6 buffers.

The 10 mg/mL samples were re-run using the same method but different columns to see if any column would give better separation of the impurity peaks or better resolution of the main peak and impurity peaks. Two columns are used were (i) Zorbax 300SB-CN Rapid resolution 4.6×50 mm, 3.5 μm; and (ii) Zorbax 300SB-C3 Rapid resolution 4.6×50 mm, 3.5 μm.

The chromatograms of these two columns were compared with the chromatograms of the original column (Zorbax SB-C8, 5 μm). The results from the various columns were very much the same. With the CN column, there was no shoulder front of the main peak; a little better for the impurity peak resolution; but peak separation was not as good because the main peak is closer to the impurity peak. With the C3 column, the peaks were separated better, but still the shoulder peak was not shown as with the C8 column. So, the decision was to stay with the C8 column for the short method that gives better peak resolution and peak separation.

Example 2

Fine Tuning of Formulation pH

Based on the initial results, it appeared that pH 7 was the best pH for further formulation development. More experiments were designed to further fine tune the pH.

25 mg/mL samples were prepared in 25 mM $Na_3PO_4$ and 25 mM NaCitrate buffers of pH 6.5, 7.0, and 7.5 and 0.15 M NaCl pH 6.5, 7.0, and 7.5. The pHs were difficult to titrate. Accordingly, the pHs were approximate, not exact.

At this time, we were also looking for a better separation between the impurity peaks and the main peak. So, LC method was slightly changed and three columns were tried to choose the best one that could give the best separation. The three columns were: (i) Zorbax 300SB C8 Rapid resolution 4.6×100 mm, 3.5 μm; (ii) Epic Polar 3 μm 120A, 4.6×100 mm; and (iii) Zorbax SB C18 Rapid resolution 4.6×75 mm, 3.5 μm The HPLC method was as follows: ramp up from 15% ACN to 75% ACN in 10 minutes, hold for 5 minutes, re-equilibration for 5 minutes and end at 20 minutes. Only the $3^{rd}$ column—Zorbax C18 give the best separation. So, the decision at this point was to go with Zorbax SB C18 Rapid resolution to analyze the 25 mg/mL samples of buffers pH 6.5, 7, and 7.5.

25 mg/mL samples were run for T0, and T1D using this column and longer gradient method for better peak separation. After that, they were saved in the HPLC auto sampler at 40° C. over the weekend for future checking of degradation at 4 days. The separation conditions were: (a) Column: Zorbax SB C18 Rapid Resolution, 4.6×75 mm, 3.5 μm; (b) Mobile phase: A: 0.1% Perchloric Acid; B: Acetonitrile; (c) Mobile phase gradient: 15% ACN to 75% ACN in 20 minutes, drop back to 15% ACN at 20.1 minutes, and end at 21 minutes; (d) Column temperature: 60° C.; (e) Sampler temperature: 40° C.; (f) Flow rate: 1 mL/min; (g) Injection volume: 5 μl; and (h) Run time: 21 minutes.

The 25 mg/mL samples in 25 mM buffers of pH 6.5, 7, and 7.5 were re-run with the longer column (C18) and long gradient method for 4 day time point. Samples of 10 mg/mL from 50° C. oven were also re-run for 4 week time point using the original method—shorter column with shorter method when the 25 mg/mL samples were done injection. Based on the results of 25 mg/mL samples, the best buffer appeared to be pH 6.5 buffer and similar conclusion were made for the 10 mg/mL samples except, the viscosity of buffers pH 7 is the best (the least viscose). At this point, the 25 mg/mL samples were still fine (not viscose). At this time, we were done with the 10 mg/mL samples. They were stored in refrigerator for later uses. Next, we ran 10 days experiment for 25 mg/mL samples at 40° C. in auto sampler.

The 25 mg/mL samples in 25 mM buffers of pH 6.5, 7, and 7.5 with the C18 column and long method for 1 week time point were re-run. We then, re-ran them again for 10 day time point. At this point, with all the chromatograms printed out and compared, it appeared that the 25 mM NaCitrate buffer pH 6.5 (with 0.0875 M NaCl), and 25 mM $Na_3PO_4$ buffer pH 7.0 (with 0.085 M NaCl) were the best candidates in terms of impurity level and viscosity to go forward to the final phase.

In the next step we added carbohydrate to the buffer to enhance the stabilization of the TNF inhibitor.

Example 3

Solution Gelation/Viscosity

In an attempt to reduce gelation or viscosity, we added carbohydrate to the formulation.

Seven carbohydrates were chosen for the experiment. They were: D-Manitol, Sucrose, D(+)-Trehalose Dihydrate, PEG 400, PEG 1000, Benzyl Alcohol (only this was not a true "carbohydrate"), and Glycerin. Five and ten percent of each of these materials were added to the phosphate pH 7 and citrate pH 6.5 buffers (without NaCl). Except for the benzyl alcohol which was only added 0.5% and 1.0% to the buffers. Then, 1 mL of 25 mg/mL solutions were prepared in HPLC vials using the stock solution and the buffers with carbohydrates just prepared. Including the controls, which were only buffers, and the buffers with the additional stabilizers (carbohydrates and Benzyl Alcohol), total of 30 samples were prepared. These samples were stored at 40° C. in the HPLC auto sampler.

3-Days analysis of those samples gave very good looking chromatograms. At this point, the glycerin, PEG 400, PEG 1000 looked the best. The mannitol looked the worst. Additional testing of 1 week analysis and 18 days analysis was performed.

Data was put together after the 18 days analysis and the conclusion at this point were: (i) Benzyl alcohol was the worst excipient to use for both citrate at pH 6.5 and phosphate pH 7.0 to stabilize the polypeptide because the polypeptide was getting low day after day at 40° C.; (ii) Glycerin was the second worst to use because it gave bigger impurity peaks; (iii) PEG1000 was probably the best carbohydrate to use to stabilize the protein in this case; (iv) even though there was not much different in term of peak impurity height and area, 5% carbohydrate worked probably better that 10% carbohydrate; (v) pH 6.5 and 7.0 buffers are not much different—however, pH 6.5 citrates appeared a little better (lower impurity peaks); (vi) the viscosity of all the samples was very good—with the samples appearing clear and not any thicker than that at the beginning.

24 day analysis results were pretty much the same as in the previous experiments. The viscosity was not much different with the eye ball check. So, the decision was to check the viscosity of some (old) 10 mg/mL samples. Samples were 10 mg/mL XENP 1595 in 5 mM $Na_2PO_4$ pH 6 (7.0 cp), 10 mg/mL XENP 1595 in 25 mM $Na_2HPO_4$ pH7 (3.5-4.0 cp), 10 mg/mL XENP 1595 in 0.15 M NaCl pH7 (5-6 cp).

The 31 day analysis results were as follows: (i) PEG1000 was probably the best in term of peak height and lowest impurity peak; (ii) Benzyl alcohol was the worst in the same reasons; (iii) In term of viscosity, sucrose, trehalose, glycerin, and manitol were less viscos than PEG4000 and PEG1000, while at this point benzyl alcohol was the most viscous, followed by PEG1000, and then PEG400; (iv) Mannitol was OK in term of viscosity but it generated the highest impurity peak; (v) Citrate pH 6.5, 5% sucrose, trehalose, and glycerin were better in 10% solution; phosphate pH 7, 5% or 10% solutions, were not much different; (vi) Between citrate and phosphate buffers, the peak height of citrate is only slightly higher.

When the heights of each single file were pulled and recorded for more accurate data, the following conclusions were made: (i) with phosphate buffers, pH 7, data were more consistent in terms of peak height for both 5% and 10% solutions.

At this time, the four best candidates were considered to be sucrose, trehalose, glycerin, and mannitol, based on the peak height of the main peak, impurity peaks, and their viscosity (eye ball check).

Viscosity of the four best candidates was measured using the Cambridge Viscometer. However, the samples had a lot of bubbles, and the machine could not run the samples. No reading was shown for these samples.

So 50, 60, 70, and 80% Glycerin in water were used as standards to check for the viscosity and were compared with the 4 candidate buffers (shake and eye-ball check). It looked like the viscosity of these buffers is close to 60%-70% of Glycerin which has viscosity of 10-14 cp.

At this point, the conclusion was made that phosphate buffer at pH 7 with one of sucrose, trehalose, glycerin and mannitol provides the best solution viscosity and chemical stability.

Example 4

Further Tuning by Differential Scanning Calorimetry

Experiments were then performed to determine suitable salts for the formulation to minimize gelation or viscosity. A high viscosity may affect delivery by an infusion devise, such as a Medtronic SynchroMed II infusion system. DSC (Differential Scanning calorimetry) was used in an attempt to find out the stability of the protein in different buffers with different stabilizers.

While waiting for the chemicals and parts for DSC experiment, 6 weeks of HPLC analysis was done for more data point on 25 mg/mL solutions. After this analysis, all the mg/mL XENP 1595 samples containing carbohydrates were saved in 37° C. incubator for later research purpose. The viscosity at this point was very similar to the previous experiments at 1 month, except that it became evident that samples with 10% carbohydrate were much more viscous than samples with 5% carbohydrate for both phosphate pH 7 and citrate pH 6.5. Citrate buffers were more viscous than phosphate buffers for both 5% and 10% carbohydrate. Accordingly, at this point, phosphate buffer at pH 7 was considered the lead candidate for the formulation.

DSC was run for 50 mg/mL XENP 1595 samples in 21 different buffer solutions including: (i) $Na_2HPO_4$ plus 0.9% NaCl, $Na_2HPO_4$ plus 2% NaCl, $Na_2HPO_4$ plus 5% NaCl; (ii) $Na_2HPO_4$ plus 0.9% KCl, $Na_2HPO_4$ plus 2% KCl, $Na_2HPO_4$ plus 5% KCl, $Na_2HPO_4$ plus 0.9% $MgCl_2$, $Na_2HPO_4$ plus 2% $MgCl_2$, $Na_2HPO_4$ plus 5% $MgCl_2$; (iii) $Na_2HPO_4$ plus 2% Sucrose, $Na_2HPO_4$ plus 5% Sucrose, $Na_2HPO_4$ plus 10% Sucrose; (iv) $Na_2HPO_4$ plus 2% Trehalose, $Na_2HPO_4$ plus 5% Trehalose, $Na_2HPO_4$ plus 10% Trehalose; (v) $Na_2HPO_4$ plus 2% Sorbitol, $Na_2HPO_4$ plus 5% Sorbitol, $Na_2HPO_4$ plus 10% Sorbitol; and (vi) $Na_2HPO_4$ plus 2% Glycerin, $Na_2HPO_4$ plus 5% Glycerin, $Na_2HPO_4$ plus 10% Glycerin.

Triplicates were run for each sample. The stability of the protein was assessed by the highest melting temperature. The results were as follows: (i) 2% NaCl was the best ionic strength to stabilize the protein (melting temperature=65° C.); (ii) KCl and $MgCl_2$ did not have much effect after 2% (melting temperature for 0.9% KCl is 64.5° C., 2% KCl is 63° C., 5% KCl is 62° C., 0.9% $MgCl_2$ is 63.5° C., 2% $MgCl_2$ is 61.5° C., and 5% $MgCl_2$ is 62° C.); (iii) 5% Sucrose and 5% Trehalose worked best in stabilizing the protein, and they were very compatible, very close result (melting temperature=65.9° C. and 66° C. respectively)—they are also well established pharmaceutical excipients—so either could be chosen.

With all the results collected thus far, we decided to choose trehalose as the carbohydrate for use in the formulation for the implantable infusion device.

Example 5

Final Formulation for Study with Infusion Device

To characterize the stability of the formulation in a Medtronic, Inc. SynchroMed II implantable infusion device, a formulation with phosphate buffer at pH 7 and trehalose was prepared.

10 and 15 mg/mL XENP 1595 was prepared in a solution of 5% trehalose in 25 mM $Na_2HPO_4$ buffer plus 0.154 M ionic strength (0.098M NaCl), pH 7.00. The buffer was filtered with Nalgene 0.2 μm filtration system. And the solutions were stored in sterile bottles.

The resulting compositions were introduced to the reservoir of the SynchroMed II infusion devices for testing at 2 speeds: 200 and 400 μL/day for the cycle of 28 days stored at 37° C. in humidified chambers. Samples were collected at different time points and saved in refrigerator until done. The samples were then analyzed by RP (reverse phase) HPLC.

The solution viscosity measurement results were as follows: (i) XenP1595 (10 mg/mL), Cycle 1, Group 1, Pump 2, Week 4=1.32 cP; (ii) XenP1595 (15 mg/mL), Cycle 1, Group 2, Pump 4, Week 4=1.87 cP; (iii) XenP1595 (10 mg/mL), Cycle 2, Group 1, Pump 2, Week 4=1.41 cP; and (iv) XenP1595 (15 mg/mL), Cycle 2, Group 2, Pump 4, Week 4~2.00 cP.

For the last sample (15 mg/mL cycle 2, G2, P4, W4), the reading was only estimated because it did not go to completion. As it started running the values fluctuating around 2 cP. However, at the final print out the reading was at 0.00 cP. This sample was run three times, and each time the results were the same. So, the value around 2.00 cP was recorded.

After one month, only one impurity peak showed a substantial increase of about 4%. However, the increase for the control was also about 4% for the same peak. Thus, the implantable infusion device does not appear to cause any additional increase in impurities.

Similarly, after one-month refill of the infusion device, only one impurity showed a substantial increase of about 2%. The increase for the control (not placed in infusion device) was 4.5%. Thus, the implantable infusion device does not appear to cause any additional increase in impurities.

Example 6

Viscosity Measurements

Viscosity measurements of various fluid compositions were taken. The results are as follows:

a. XenP1595 (10 mg/mL), Cycle 1, Group 1, Pump 2, Week 4=1.32 cP
b. XenP1595 (15 mg/mL), Cycle 1, Group 2, Pump 4, Week 4=1.87 cP
c. XenP1595 (10 mg/mL), Cycle 2, Group 1, Pump 2, Week 4=1.41 cP
d. XenP1595 (15 mg/mL), Cycle 2, Group 2, Pump 4, Week 4~2.00 cP For the last sample (15 mg/mL cycle 2, G2, P4, W4), the reading was only estimated because it did not go to completion. The values fluctuated around 2 cP at the start. However, when observed at the end a reading of only 0.00 cP was observed. The viscosity measurement assay was run three times for this sample, and each time the results were the same. So, a value of around 2.00 cP was recorded for this sample.

Thus, embodiments of TNF INHIBITOR FOR USE IN IMPLANTABLE INFUSION DEVICES are described. Those skilled in the art will recognize that the embodiments described herein may be altered without departing from the true spirit and scope of the disclosure.

What is claimed is:

1. An injectable formulation, comprising:
   between 5 mg/ml and 500 mg/ml of a tumor necrosis factor (TNF) inhibitor polypeptide having one or more of the following amino acid substitutions VIM; R31C; C69V; Y87H; C101A; and A145R, relative to a 157 amino acid long N-terminal portion of the amino acid sequence of SEQ ID NO:1;
   between 10 mM and 25 mM of a phosphate or citrate buffer;
   between 5% and 10% of a carbohydrate; and
   optionally NaCl, wherein the combined ionic strength of the buffer and the optional salt is an equivalent ionic strength of between 0.1M and 0.2M NaCl,
   wherein the formulation has a pH of between 6 and 7, is fluid at room temperature and at 37° C., and has a viscosity of 10 centipoise or less at room temperature, and
   wherein the formulation is configured to be delivered via an implantable infusion device.

2. The formulation of claim 1, wherein the TNF inhibitor polypeptide is conjugated to a polymer and has a molecular weight of between 5 kilodaltons and 50 kilodaltons.

3. The formulation of claim 1, wherein the TNF inhibitor polypeptide is conjugated to a polymer and has a molecular weight of between 7 kilodaltons and 20 kilodaltons.

4. The formulation of claim 1, wherein the TNF inhibitor polypeptide is conjugated to a polymer and has a molecular weight of about 10 kilodaltons.

5. The formulation of claim 1, wherein the polypeptide is conjugated to polyethylene glycol.

6. The formulation of claim 1, wherein the TNF inhibitor polypeptide comprises each of the following substitutions: V1M; R31C; C69V; Y87H; C101A; and A145R.

7. The formulation of claim 1, wherein the TNF inhibitor polypeptide is conjugated to polyethylene glycol at the cysteine at position 31.

8. The formulation of claim 1, wherein the TNF inhibitor polypeptide is present in the formulation at a concentration of between 10 mg/ml and 25 mg/ml.

9. The formulation of claim 1, wherein the carbohydrate is trehalose or sucrose.

10. The formulation of claim 1, wherein the carbohydrate is trehalose.

11. The formulation of claim 1, wherein the combined ionic strength of the buffer and the optional salt is an equivalent ionic strength of 0.15M.

12. The formulation of claim 1, wherein the formulation has a viscosity of between 1 centipoise and 9 centipoise at room temperature.

13. The formulation of claim 1, wherein the formulation has a viscosity of between 1 centipoise and 5 centipoise at room temperature.

14. The formulation of claim 1, wherein the formulation has a viscosity of between 1 centipoise and 3 centipoise at room temperature.

15. The formulation of claim 1, wherein the formulation has a viscosity of between 1 centipoise and 2.5 centipoise at room temperature.

16. An injectable formulation, comprising:
   between 5 mg/ml and 500 mg/ml of a tumor necrosis factor (TNF) inhibitor polypeptide having the following amino acid substitutions VIM; R31C; C69V; Y87H; C101A; and A145R, relative to a 157 amino acid long N-terminal portion of the amino acid sequence of SEQ ID NO:1, wherein the TNF inhibitor polypeptide is conjugated to polyethylene glycol at the cysteine at position 31 and has a molecular weight of between 7 kilodaltons and 20 kilodaltons;

between 10 mM and 25 mM of a phosphate or citrate buffer;

between 5% and 10% of a carbohydrate, wherein the carbohydrate is selected from the group consisting of trehalose and sucralose; and optionally NaCl, wherein the combined ionic strength of the buffer and the optional salt is an equivalent ionic strength of between 0.1M and 0.2M NaCl, wherein the formulation has a pH of between 6 and 7, is fluid at room temperature and at 37° C., and has a viscosity of 10 centipoise or less at room temperature, and wherein the formulation is configured to be delivered via an implantable infusion device.

17. An injectable formulation, comprising:

between 5 mg/ml and 500 mg/ml of a tumor necrosis factor (TNF) inhibitor polypeptide having the following amino acid substitutions: VIM; R31C; C69V; Y87H; C101A; and A145R, relative to a 157 amino acid long N-terminal portion of the amino acid sequence of SEQ ID NO:1;

between 10 mM and 25 mM of a phosphate or citrate buffer;

between 5% and 10% of a carbohydrate; and optionally NaCl, wherein the combined ionic strength of the buffer and the optional salt is an equivalent ionic strength of between 0.1M and 0.2M NaCl, wherein the formulation has a pH of between 6 and 7, is fluid at room temperature and at 37° C., and has a viscosity of 10 centipoise or less at room temperature, wherein the formulation is stable at 37° C. for 30 days or more, and wherein the formulation is configured to be delivered via an implantable infusion device.

* * * * *